United States Patent [19]
Thundat et al.

[11] Patent Number: 6,096,559
[45] Date of Patent: Aug. 1, 2000

[54] MICROMECHANICAL CALORIMETRIC SENSOR

[75] Inventors: Thomas G. Thundat; Mitchel J. Doktycz, both of Knoxville, Tenn.

[73] Assignee: Lockheed Martin Energy Research Corporation, Oak Ridge, Tenn.

[21] Appl. No.: 09/039,707

[22] Filed: Mar. 16, 1998

[51] Int. Cl.[7] .................................................. G01N 25/20
[52] U.S. Cl. .................... 436/147; 422/51; 422/82.12; 436/34
[58] Field of Search ................................... 422/51, 82.12; 436/147, 34

[56] References Cited

U.S. PATENT DOCUMENTS

| | | |
|---|---|---|
| 4,591,550 | 5/1986 | Hafeman et al. . |
| 4,963,815 | 10/1990 | Hafeman . |
| 5,440,920 | 8/1995 | Jung et al. . |
| 5,445,008 | 8/1995 | Wachter et al. . |
| 5,719,324 | 2/1998 | Thundat et al. . |
| 5,739,425 | 4/1998 | Binnig et al. . |
| 5,807,758 | 9/1998 | Lee et al. . |
| 5,831,181 | 11/1998 | Majumdar et al. . |

OTHER PUBLICATIONS

Berger et al., Sens. Their Appl. VIII, Proc. Conf 8th (1997), 71–76, edited by Augousti et al., published by Instittue of Physics Publishing, Bristol, 1997.
Gimzewski et al., Chem. Phys. Lett. (1994), vol. 217, Nos. 5–6, pp. 589–594, 1994.
Chemical Abstracts (Columbus, Ohio) Abstract No. 128:63264: Berger et al., Sens. Their Appl. VIII, Proc. Conf., 8th (1997), 71–76, edited by Augousti et al., published by Institute of Physics Publishing, Bristol, UK, 1997.

*Primary Examiner*—Jan Ludlow
*Attorney, Agent, or Firm*—Hardaway/Mann IP Group

[57] ABSTRACT

A calorimeter sensor apparatus is developed utilizing microcantilevered spring elements for detecting thermal changes within a sample containing biomolecules which undergo chemical and biochemical reactions. The spring element includes a bimaterial layer of chemicals on a coated region on at least one surface of the microcantilever. The chemicals generate a differential thermal stress across the surface upon reaction of the chemicals with an analyte or biomolecules within the sample due to the heat of chemical reactions in the sample placed on the coated region. The thermal stress across the spring element surface creates mechanical bending of the microcantilever. The spring element has a low thermal mass to allow detection and measuring of heat transfers associated with chemical and biochemical reactions within a sample placed on or near the coated region. A second surface may have a different material, or the second surface and body of microcantilever may be of an inert composition. The differential thermal stress between the surfaces of the microcantilever create bending of the cantilever. Deflections of the cantilever are detected by a variety of detection techniques. The microcantilever may be approximately 1 to 200 μm long, approximately 1 to 50 μm wide, and approximately 0.3 to 3.0 μm thick. A sensitivity for detection of deflections is in the range of 0.01 nanometers. The microcantilever is extremely sensitive to thermal changes in samples as small as 30 microliters.

25 Claims, 5 Drawing Sheets

MICROMECHANICAL CALORIMETRIC SENSOR

CROSS-REFERENCE TO RELATED APPLICATIONS

The invention relates to the following patents, Wachter et al., U.S. Pat. No. 5,445,008, issued Aug. 29, 1995, and Thundat et al., U.S. Pat. No. 5,719,324, issued Feb. 17, 1998, which are herein incorporated by reference.

STATEMENT AS TO RIGHTS TO INVENTIONS MADE UNDER FEDERALLY-SPONSORED RESEARCH AND DEVELOPMENT

The United States Government has certain rights in this invention pursuant to contracts numbers DE-AC05-96OR22464 and DE-AC05-84OR21400, between the U.S. Department of Energy and Lockheed Martin Energy Research Corporation.

BRIEF SUMMARY OF THE INVENTION

The invention relates generally to calorimetric sensor technology for detecting thermal changes in a monitored media, and more particularly to utilizing microcalorimetry to detect thermal changes due to chemical reactions of biomolecules while in a sample of monitored media.

BACKGROUND OF THE INVENTION

Calorimetry measurements are commonly utilized in biophysical and biochemical studies to determine energy changes as indications of biochemical reactions in a media. Prior techniques for measurements include using electrodes, thermopiles, optical techniques, and microcalorimeters for measurements within a sampled media. There is a great interest in developing ultra-miniature microcalorimeter devices that require very small volumes of sampled media for accurate detection and measuring of biochemical reactions on, or in close proximity to, the microcalorimeter.

In Thundat et al., U.S. Pat. No. 5,719,324, a piezoelectric transducer is disclosed that is fabricated with a cantilever having a spring element treated with a chemical having an affinity for a specific vapor phase chemical. An oscillator means maintains a resonant vibrational frequency during detection of a chemical, with changes in resonant frequency indicating amounts of targeted chemical detected in the monitored atmosphere.

In Wachter et al., U.S. Pat. No. 5,445,008, a mass microsensor is disclosed that is fabricated with a microcantilever, that oscillates due to a piezoelectric transducer, with a chemical coating on the microcantilever that absorbs a targeted chemical from the monitored atmosphere. The resonant frequency of the microcantilever is analyzed to determine changes that indicate amounts of targeted chemical detected in the monitored atmosphere.

In Marcus et al., U.S. Pat. No. 5,475,318, a microprobe is disclosed that includes a microcantilever, a base, a probe tip projecting from the base, and a heating element that heats the probe tip, which comes into contact with a material to be investigated.

In Hafeman, U.S. Pat. No. 4,963,815, a device and method is provided for determining an analyte by measuring a redox potential-modulated photoinducing electrical signal from an electronically conducting layer on a semiconductor device.

In Kolesar, U.S. Pat. No. 4,549,427, a chemical nerve agent detector is disclosed that includes a transducer having two microcantilever oscillators. The active microcantilever of the two microcantilevers has a chemically selective substance that absorbs chemical nerve agents from the atmosphere, with modifications in the oscillation of the active microcantilever, and comparisons are made between the frequency of the active cantilever and the reference cantilever.

The above described methods and devices of measuring chemical and micromechanical parameters in sampled media have numerous shortcomings. The prior art does not provide for detecting and monitoring by an apparatus of low thermal mass of heat exchanges of chemical reactions related to biomolecules as the reactions occur in a sample of monitored media. Thus there exists room for improvement within the art. The subject invention provides a novel approach to sampling of thermal changes in a media utilizing extremely small sample volumes of media.

SUMMARY OF THE INVENTION

It is an object of this invention to provide a detection method for chemical reactions in a sampled media.

It is a further object of this invention to provide a microcalorimetry method for detection of heat exchanges related to chemical reactions and reactions between biomolecules on the sensor or with the sensor in close proximity to the biomolecules in a sampled media.

It is an additional object of this invention to provide an ultra-miniature microcalorimeter having a low thermal mass.

It is a further and more particular object of this invention to provide a ultra-miniature microcalorimeter that provides extremely high sensitivity and low power requirements.

These and other objects of the invention are accomplished by an apparatus and a method for detecting and measuring heat exchanges of biochemical reactions in a sampled media, including: a calorimeter comprising a transducer base having at least one cantilevered spring element attached to the base, with the spring element having at least one surface with a coated region, the coated region having at least one chemical attached, the chemical having a first coefficient of thermal expansion, and the spring element having an overall low thermal mass. The coated region on the spring element has a chemical material which has an affinity for the biomolecule in the sample placed on the coated region, with the biomolecule and the chemical on the coated region participating in a biochemical reaction, allowing detection and measuring of heat exchanges in a sample placed on the spring surface. The spring element has a second coefficient of thermal expansion associated with a second surface and/or the spring element, the second coefficient being different than the first coefficient of thermal expansion. The apparatus and the method has a means for detection of the changes in deflection of the cantilevered spring element created by the thermal stresses created on the coated region of the first surface which forces a deflection of the microcantilever. The microcantilever is small in size to provide a low thermal mass and to provide sensitivities in the sub-nanometer range for deflections in response to thermal stresses on the spring element in proportion to heat exchanges between the biomolecules within a sample of media placed on or near the spring element.

Thus, the objects of the invention are accomplished by the apparatus and the method for measuring thermal changes associated with biochemical reactions within a sample of media placed on a cantilevered spring element as described herein.

BRIEF DESCRIPTION OF THE DRAWINGS

The invention's features and advantage will become apparent from a reading of the following detailed description, given with reference to the various figure of drawing, in which.

DETAILED DESCRIPTION OF THE PREFERRED EMBODIMENT

Figure 1:
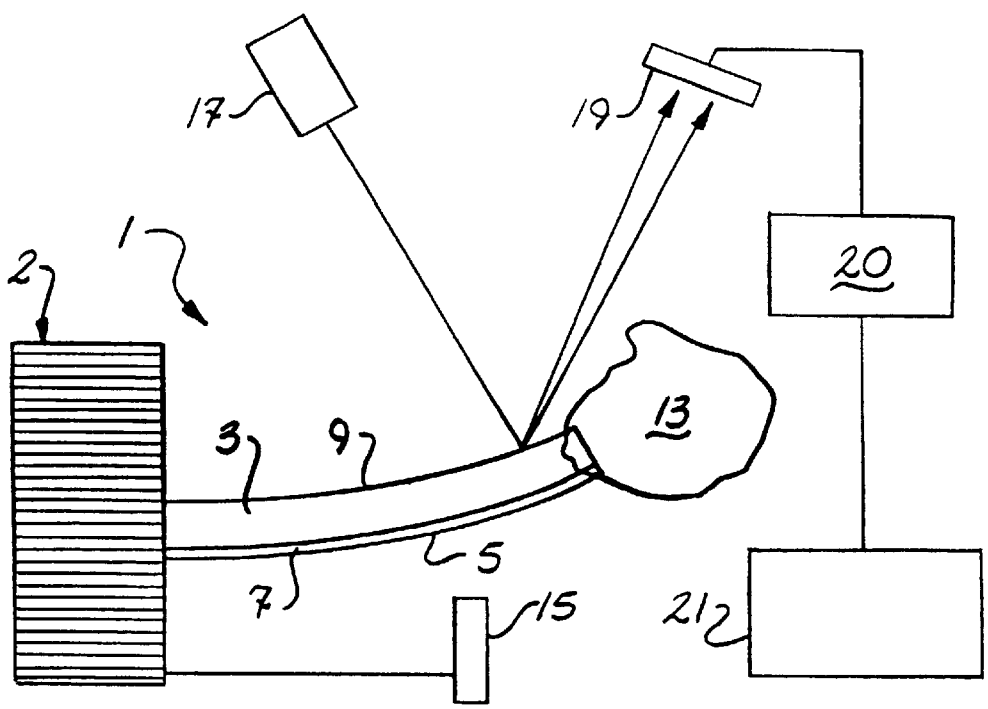
FIG. 1 is a pictorial schematic of one alternate embodiment of the microcantilever assembly and bending detection assembly of the present invention.

In accordance with this invention, it has been found that a detection method and a calorimeter sensor apparatus is needed that is ultra miniaturized and is extremely sensitive to slight changes in the thermal content of a sampled media containing biomolecules. The invention is capable of measuring changes in the thermal energy of material on a microcantilevered spring element, or in close proximity to the surface of the microcantilevered spring element, which accurately measures the enthalpy of chemical, biochemical and physical reactions in the media being sampled. The invention utilizes bimaterial coatings or multilayered microcantilevers incorporated into an ultra-miniature microcalorimeter sensor apparatus. A method of detecting and monitoring thermal changes due to chemical reactions in a sample by means of the bending of a microcantilevered spring element is disclosed. The movement of the microcantilevered spring element is detected using a detection means that provide detection sensitivities in the sub-nanometer range for deflection measurements. The invention requires less than approximately 30 microliters or as little as a nanoliter of sampled media for accurate measurements.

In accordance with FIGS. 1–4, an embodiment for the present invention is a calorimetric sensor apparatus 1 comprising a transducer base 2 having at least one microcantilevered spring element 3 (also referenced as a microcantilever), with or without a separate reference microcantilevered spring element 15, and additional spring elements as needed for determining heat transfer of biochemical reactions related to biomolecules in a volume of a sample 13 of monitored media. Spring element 3 may have the dimensions of approximately 1.0 to approximately 200 $\mu$m long, approximately 1.0 to 50 $\mu$m wide, and approximately 0.1 $\mu$m to 3.0 $\mu$m thick. The alternate dimensions are approximately 50 $\mu$m to approximately 200 $\mu$m long, approximately 10 $\mu$m to approximately 30 $\mu$m wide, and approximately 0.3 $\mu$m to approximately 3.0 $\mu$m thick.

Each of the above dimensions may be varied to configure the spring element 3 to detect the thermal changes within the media on a first surface 5 of the microcantilever 3. A second surface 9 opposes the first surface. Either surface 5 or 9 may have a chemical coating on a coated region 7 for detection and measuring of heat transfer of targeted biochemical reactions. The thickness of the spring element 3 is variable depending on the number of chemical coatings and materials applied to the surfaces 5, 9. The micron size of the spring element 3 allows for a low thermal mass of the combination of the spring element, chemical coatings, and other materials attached to the spring element surfaces 5, 9.

Spring element 3 extends outward from the base 2 as shown in FIG. 1. The calorimetric sensor apparatus 1 may consist of a plurality of microcantilevered spring elements 3 attached to the calorimeter apparatus 1. Reference microcantilever 15, if utilized, is located in close proximity to spring element 3. Each microcantilever may be constructed of materials such as metals, ceramics, polymers, quartz, silicon nitride, silicon, silicon oxide, aluminum oxide, tantilum pentoxide, germanium, germanium dioxide, gallium arsenide, zinc oxide, or any semiconductor material, to provide for low cost and for mass production by techniques commonly utilized in the semiconductor industry.

Spring element 3 can be approximately rectangular as shown in FIGS. 1–5. The shape of the microcantilevered spring element 3 may be modified according to the thermal changes that are being monitored. The coated region having a chemical coating and/or additional materials attached may be located at the distal end (see FIG. 4) of the spring element 3, or at the proximal end to the base 2 (not shown), and the chemical coating and/or additional materials may be coated or treated on any surface 5, 9 of the spring element 3.

The spring constant of microcantilevered spring element 3 is designed to produce cantilever deflection at the sub-nanometers level. The low thermal mass of the spring element 3 having chemical coatings and/or additional materials treated on a surface, allows the spring element to deflect in response to temperature changes of $10^{-6}$ K for heat exchanges during chemical reactions of biological compounds and biochemical reactions within a sample 13 placed on the spring element 3.

The bimaterial coating 7 of surface 5 may include gold, aluminum, copper, or a silicon compound having different thermal expansion rates in response to extremely small temperature changes (approximately $10^{-6}$ K). Other coating types for coating 7 distributed on or within first surface 5, or separate coating 8 distributed on or within second surface 9 include: ceramics, polymers, silicon compounds, silicon oxide, silicon nitride, quartz, or biopolymers. The polymers or biopolymers within the coating 7, or added as a second coating 8 may include enzymes, peptides, proteins, polysaccharides, nucleic acids, carbohydrates, antibody and antigen molecules, pharmacological agents (i.e. drugs, including small organic molecules such as aspirin), and other biopolymers, and any class of biochemical compounds which react with one or more analytes or other biopolymers in a sample 13 placed on the coating 7, 8. The chemical reactions of one or more biomolecules in sample 13 produce heat transfer within, on, or in close proximity to the spring element surfaces 5, 9. The extremely small temperature changes are detectable as a result of the low thermal mass of the spring element 3, during the biochemical reactions before the heat of reaction is lost to the surrounding sample volume or the surrounding monitored media. The heat transfer on the surface of the spring element 3 that results from a temperature change in the coating 7, creates a resulting thermal stress in the coated surface 5 or 9, which results in a thermal rate of expansion of one surface of the spring element 3, forcing a deflection in the spring element 3 depending on the heat of transfer during biochemical reactions within the sample 13 placed on the spring element 3. The sample 13 of monitored media may consist of a gas a liquid analyte, or actual single biological cells, or biomolecules such as enzymes, peptides, proteins, nucleic acids, polysaccharides, carbohydrates, antibody and antigen molecules, pharmacalogical agents (i.e. drugs and small organic molecules such as aspirin), and/or other biopolymers.

Sensing microcantilever 3 may have a spring constant in the range of 0.01 to 50 Newton/meter, depending on the microcantilever dimensions. Each coating layer 7, 8 has a separate distinct spring constant which differs from the first spring constant of the microcantilever 5 without a coating. A thinner bimaterial microcantilever will provide faster responses to smaller thermal changes within the sampled media 13. Responses to forces as small as approximately a few pico Newtons are possible for the microcantilevers of the present invention, providing an advantage in sensitivity over prior calorimeter devices. Microcantilevers with force constants as small as 0.08 Newton/meter are commercially available from Park Instruments, Sunnyvale, Calif.

Sensing microcantilever 3, has a second surface 9 opposing the first surface 5. The second surface 9 may or may not have a second coating 8 (FIG. 3) distributed across the surface 9, depending on the parameters of the calorimeter apparatus 1 required for sensing thermal changes within the sampled media 13. Second coating 8, if present, may consist of a material differing in thermal expansion rates from first coating 7, such as ceramics, polymers biopolymers, metals, silicon nitride, or silica compounds. Second surface 9, or a section of first surface 5, may be reflective of light. Coating first surface 5 of sensing microcantilever 3 with a gold film, a different or a second metallic material, or a silicon nitride coating 7, allows the microcantilever 3 to be extremely sensitive to temperature variations on the first surface 5 which correlate to enthalpy changes in the monitored media 13. The coefficient of thermal expansions for gold is 14.2× $10^{-6}$/K, and for silicon nitride is $3 \times 10^{-6}$/K.

As the analyte and biomolecules on first surface 5 undergo reactions with compounds in the sample 13 of monitored media, the resulting chemical and biochemical reactions release an amount of heat into the sample. Enzyme catalyzed reactions typically may proceed with enthalpy changes in the range of approximately 20–100 kilo joules/mole. As heat is generated by biochemical reactions within the monitored media 13 on the first surface 5, the media 13 transmits heat variations to the coating 7 of gold metal or silicon nitride on first surface 5, which has a different coefficient of thermal expansion from the silicon or quartz material of sensing microcantilever 3 and second surface 9. The differing thermal expansion rates of adjacent surfaces force the microcantilever 3 to undergo bending (see FIG. 1). The bending is due to differential stress created by the differential thermal expansion of silicon or quartz of microcantilever 3, and gold material 7 (a bimetallic effect) on the first surface 5 of microcantilever 3.

The bending of the microcantilever 3, even though extremely small, can be detected by known laser optical techniques with sub-nanometer sensitivities. If laser detection is used, at least one layer on one surface, or one end of a surface of sensing microcantilever 3, must be reflective of laser light. The laser optical sensing means includes a photo diode generator 17 of laser light focused on the first surface 5 or the second surface 9 of sensor microcantilever 3, with a photodetector 19 positioned to receive the reflected laser light, with analysis of the bending of the sensing microcantilever 3 by microprocessors.

Alternative detection means are possible. These include a piezoresistive detection means, a piezoelectric detection means, a capacitive detection means, and an electron tunneling detection means, all of which are conventionally known. Each detection means determines changes in deflection of the microcantilever 3 with sensitivities comparable to the sub-nanometer sensitivity of the laser sensing means. A general discussion of deflection detection techniques coupled with microcalorimeters, and references for each alternative detection means is provided in Gimzewski et al. ("Observation of a chemical reaction using a micromechanical sensor," 217 *Chem. Phys. Lett.* 589, at 593 (1994)) herein included by reference.

The extent of bending is directly proportional, in first order, to the energy absorbed. The bending, z, due to differential stress, As, can be written as $$z = \left(\frac{tl^3}{4IE^*}\right)\Delta s \quad (1)$$

where t is the thickness, l is the length, I is the moment of inertia, and $E^* = (E_1 + E_2)/E_1 E_2$ is the effective Young's modulus of the microcantilever.

The differential stress due to thermal expansion of the materials can be written $$\Delta s \approx (E_1 \alpha_1 - E_2 \alpha_2)\Delta T \quad (2)$$

Where $\Delta T$ is the temperature change and $\alpha_1$ and $\alpha_2$ are coefficients of thermal expansion of the materials of the bimetallic strip. Therefore, by measuring the bending distance z, the change in temperature can be determined as, $$\Delta T \approx \frac{1}{3}\left[\frac{E^* b t^2}{l^3 (E_1 \alpha_1 - E_2 \alpha_2)}\right]z \quad (3)$$

where b is the width of a rectangular cantilever. The above formula applies in an ideal case where the thermal mass of the cantilever and the base of are extremely small. An assumption is that all the incident heat flux was absorbed by the cantilever and the base, resulting in a uniform temperature change. Therefore Equation 3 is only a theoretical upper limit. For a uniform heat flux, dQ/dt, the differential thermal stress is given by, $$\Delta s = \frac{(E_1 \alpha_1 - E_2 \alpha_2)}{E^*}\left(\frac{v}{\lambda t}\right)\eta\left(\frac{dQ}{dt}\right) \quad (4)$$

Where v is the volume of the cantilever, $\eta$ is the fraction of the heat flux absorbed, and $\Lambda$ is the effective thermal conductivity.

As an example of the proposed thermal sensitivity, a silicon nitride microcantilever may have dimensions of between 1 $\mu$m to 200$\mu$m length, 1 to 50 $\mu$m width, and 0.3 to about 3.0 μm thickness with a gold layer on a first surface 5. The coefficient of thermal expansions for gold and silicon nitride are $14.2\times10^{-6}$/K and $3\times10^{-6}$/K respectively. Using a laser diode and a position detector, the bending of a microcantilever can be detected with a sensitivity less than 0.01 nm. Therefore, the theoretical temperature measurement sensitivity using the microcantilever described herein is $10^{-6}$K. The present invention provides a microcantilevered spring element that has a lower thermal mass than other calorimeter sensor systems currently utilized. A general discussion of microcalorimetry utilizing oscillating microcantilevers is provided in Gimzewski et al. ("Observation of a chemical reaction using a micromechanical sensor," 217 Chem. Phys. Lett. 589, at 591–592 (1994)).

The above described microcalorimeter apparatus 1 may also be utilized for measuring absorption or adsorption of molecules on a material such as gold deposited on surface 5 of microcantilevered spring element 3 from the air or water media 13. For example, mercury will adsorb selectively on the gold coated first surface 5. The heat of reaction of the adsorption reaction will create a differential thermal stress between the first surface 5 and the spring element 3, with a resulting bending and deflection of the microcantilever 3, which can be detected by the laser light from the laser diode 17 received at the photodetector 19. The deflections of the microcantilever 3, as detected by reflected light, are analyzed by a microprocessor 21, with or without amplification 20, with deflections correlated with heat released or absorbed by chemical reactions occurring between biomolecules on or in close proximity to the chemical coating 7 on the first surface 5, and/or the second material 8 on the second surface 9.

Figure 2:
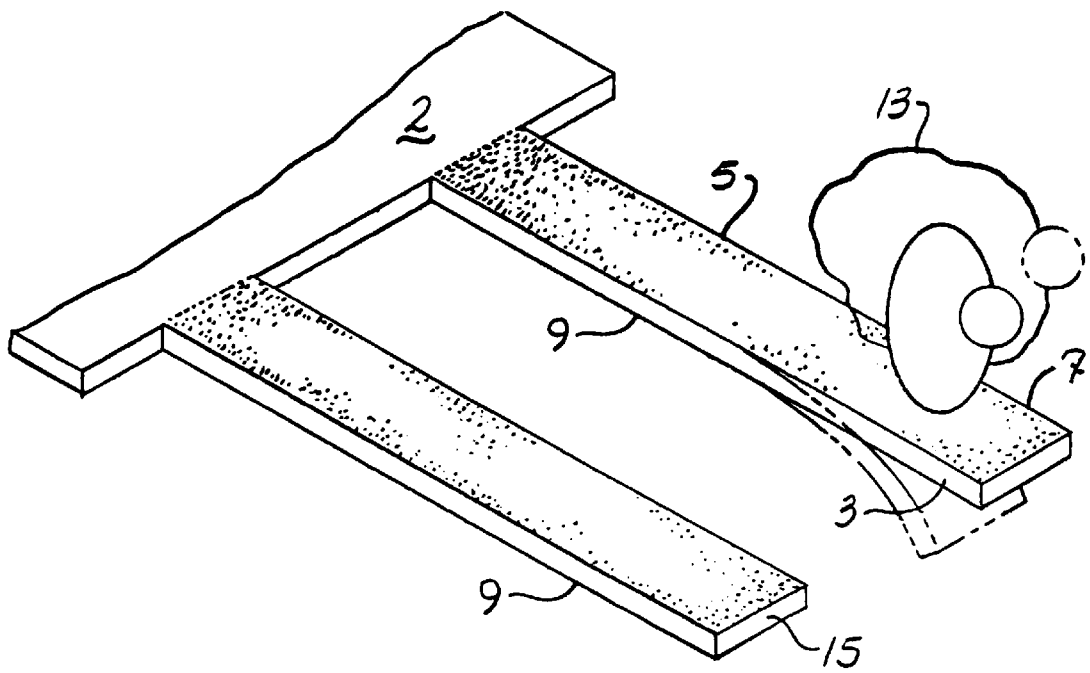
FIG. 2 is a perspective view of the present invention having a sample of monitored media in contact with the microcantilever.
Figure 3:
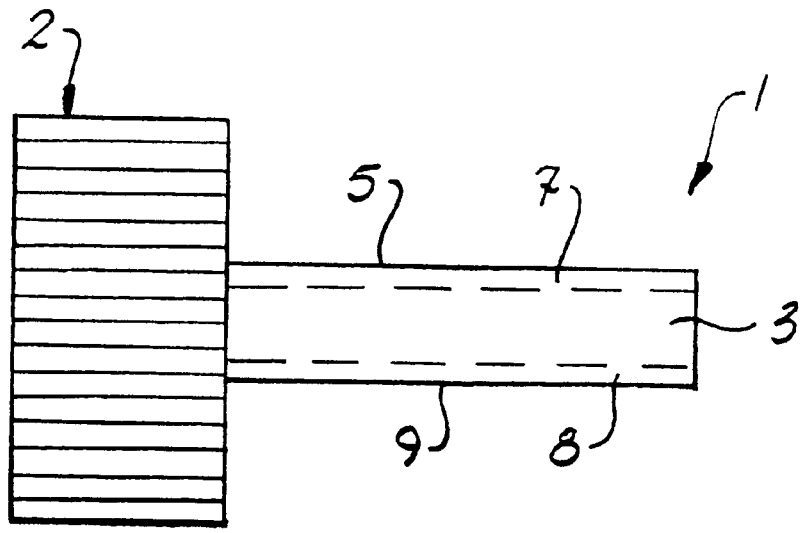
FIG. 3 is a cross-sectional side view of one alternate embodiment of the present invention having two coated surfaces.
Figure 4:
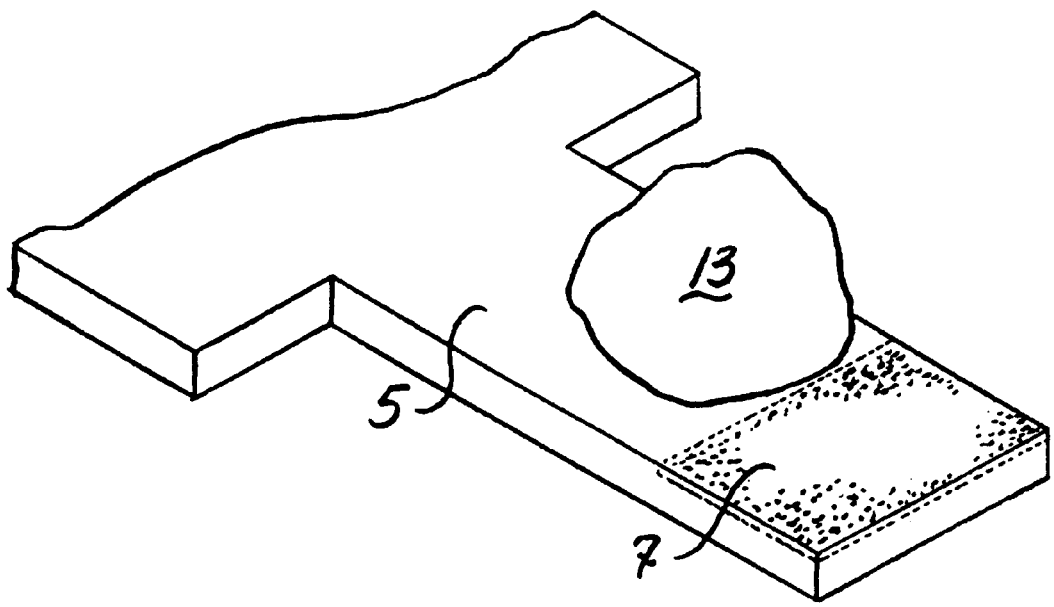
FIG. 4 is a side perspective view of one alternate embodiment of the present invention having a coated region at the distal end of the microcantilever.

An additional embodiment of the above described calorimetric sensing apparatus 1 may consist of a plurality of microcantilevered spring elements 3 with a coating 7 containing an antibody treated on a first surface 5 (FIG. 2). The sample 13 is exposed to the first surface 5, the sample 13 having analyte molecules in contact with the antibody coating 7 on the first surface 5. The analyte will adsorb on, or absorb in, appropriate materials on or in the antibody coating 7, creating heat exchanges, and the surface 5 will expand due to the generation of localized heat due to binding of the analyte to the antibody. The bending of spring element 3 may be detected by a detection means such as a laser detection method, or a similar detection method, by the measurement of a movement of spring element 3, as the adsorption sites are filled with analyte. The movement of microcantilever 3 is monitored by the laser 17 and photodetector 19. When all of the adsorption sites are filled, heat changes due to adsorption onto chemical sites will cease, with a loss of a differential thermal stress across the spring element 3, which will return to an equilibrium position. The temperature of the spring element 3 and coating 7 may be raised by heating the spring element 3 by passing current through the microcantilever by way of the transistor base. Alternatively, microcantilever 3 can be heated to a set temperature by a resistive film (not shown) deposited on the second surface 9. The temperature of the analyte in the sample 13 may be changed by heating, or another physical condition may be changed (i.e. ion concentration), of the sample 13 on the spring element 3 to change the equilibrium of the adsorption sites on the surface 5 (not shown). The thermal heat exchanges within the sample 13 being monitored is measured by the bending of the spring element 3 in comparison to the untreated reference microcantilever 15. Plotting the bending of the untreated reference microcantilever 15 as a function of deflection between spring element 3 and microcantilever 15 will provide peaks corresponding to the desorption of the analyte from the coating 7 on surface 5 of spring element 3.

Method of Detecting and Measuring

The steps of detecting and measuring thermal changes with a calorimeter sensor of chemical reactions between biomolecules in a sample of monitored media placed on or in close proximity to the present invention include: providing a transducer base; attaching at least one cantilevered a spring element to the transducer; providing the microcantilever with a base having a material that has one spring element, at least one surface on the spring element having a coated region with a chemical attached that has a thermal coefficient of expansion differing from the spring constant of the cantilever base. The coated region spring constant expands or contracts in response to the thermal changes in the sample placed on or near the surface of the spring element. A second coating of inert material may be distributed on the second surface or within the base of the microcantilever, providing a different thermal coefficient of expansion, which will deflect the spring element upon exposing of the cantilevered spring element coating(s) to the sample containing biopolymers or chemicals undergoing biochemical reactions. The sample may be placed on at least one surface of the spring element, or in close proximity to the coated region, or the spring element may be placed within or near a sample of monitored media. The deflection of the cantilever is detected by a detection means which includes: providing a photo-detecting means having a laser light source directing light at the cantilevered spring element surface. The reflected light from the cantilever surface is captured by positioning a light sensitive detector near the cantilevered spring element, the detector receiving reflected light from the cantilever surface before, during, and after bending of the microcantilever. The degree of bending is measured in reference to a neutral position of the cantilever, and a microprocessor is provided for analyzing deflection information from the measuring steps. The changes in deflection are correlated with thermal changes within the monitored media by utilizing the microprocessor and mathematical formulas to calculate the rate of thermal changes as a function of biomolecule reactions within the media and the degree of cantilever deflection when the cantilever's bending parameters are known.

Additional Embodiments

Figure 5:
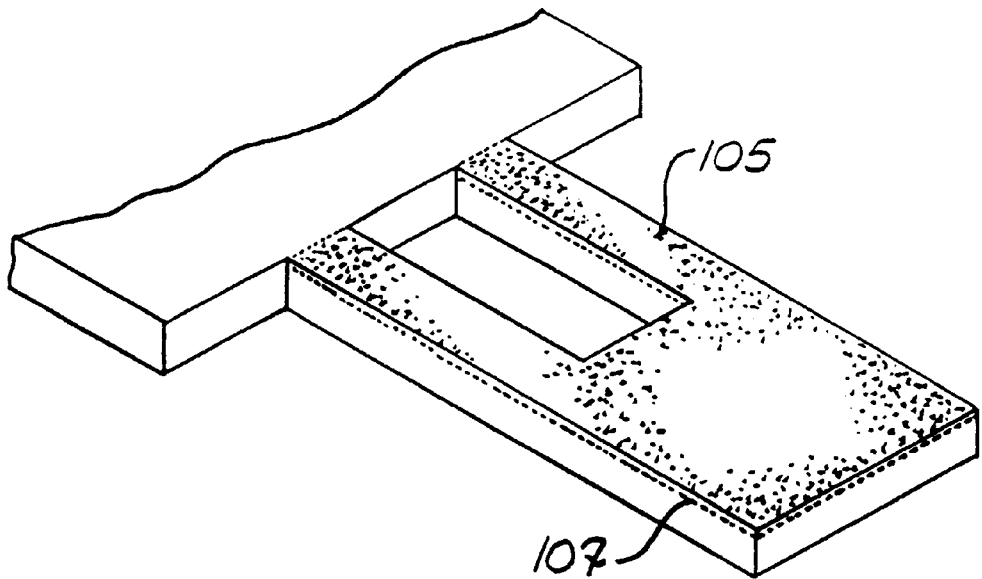
FIG. 5 is a side perspective view of another alternate embodiment of the present invention having an interior void.

As shown in FIG. 5, an alternate embodiment is spring element 103 having a rectangular shape having a central void 104 near the base 102 that serves to provide isolation of a chemical coating 107 and/or additional material on one or more of the surfaces, or on the distal end, of the spring element 103. A coating of material 107 having a first coefficient of thermal expansion is spread on part, or all of one surface of the microcantilever 103.

Figure 6:
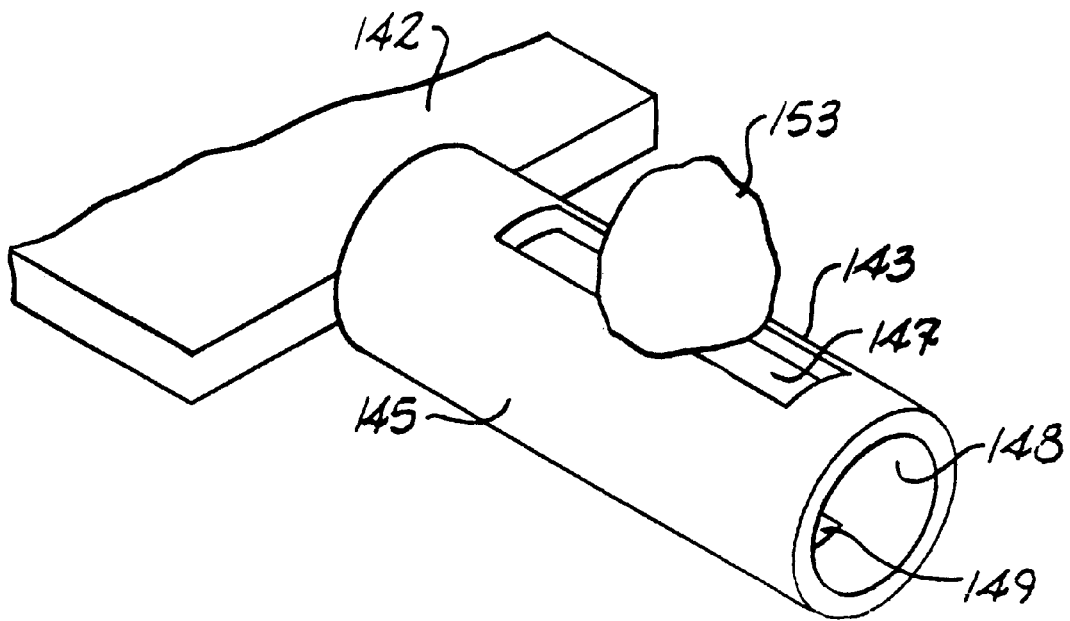
FIG. 6 is side perspective view of another alternate embodiment of the present invention in a tubular configuration.
Figure 7:
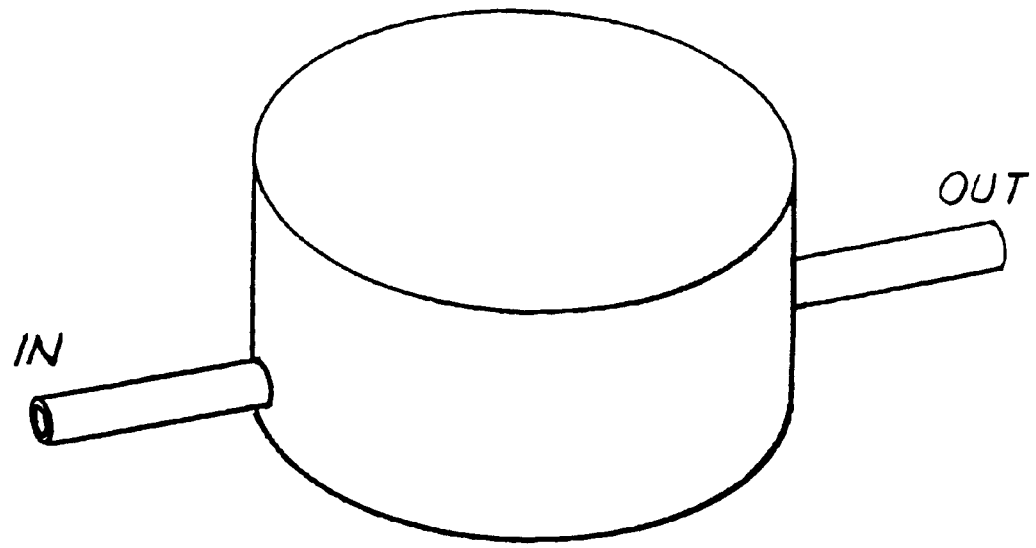
FIG. 7 is a pictorial representation of the assembled microcantilever sensor.
Figure 8:
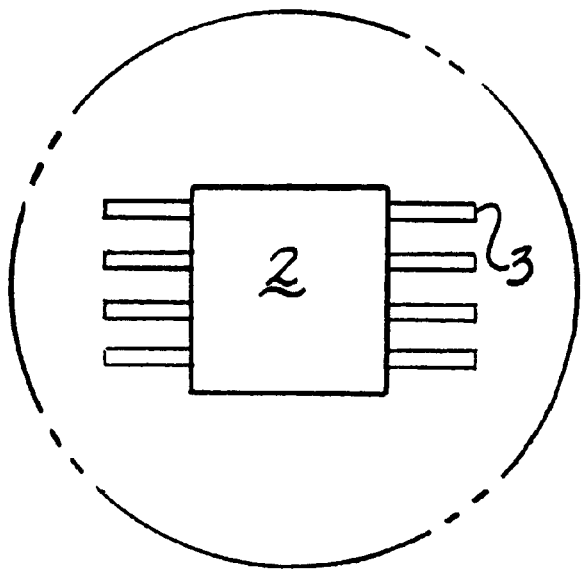
FIG. 8 is a top view of the cylindrical section of the assembled microcantilever sensor.
Figure 9:
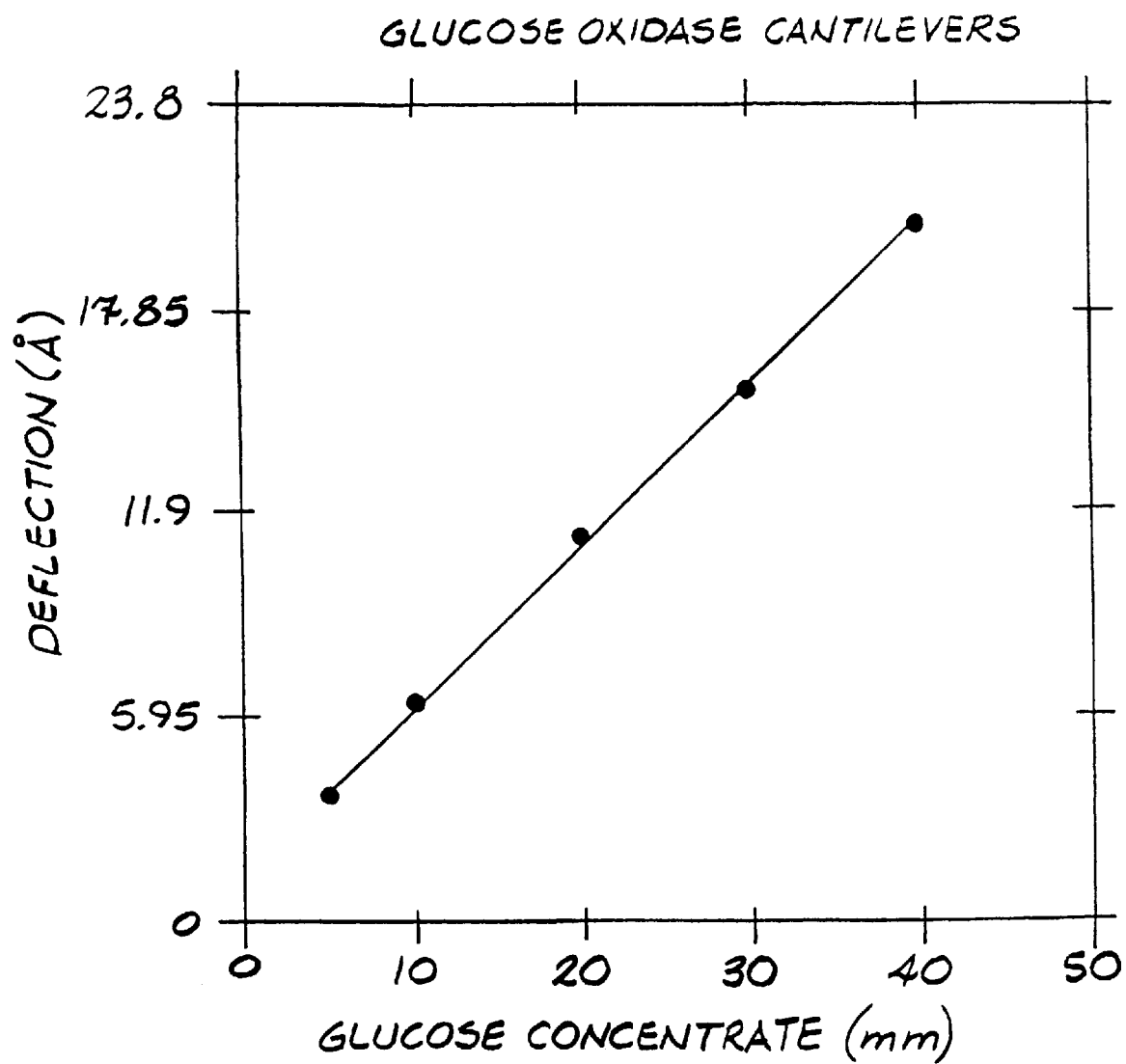
FIG. 9 is a graph which illustrates deflection of the present invention in the presence of thermal changes due to the presence of glucose in a sample of monitored media.

Another embodiment of the microcantilevered spring element includes either a cylindrical spring element, or, as shown in FIG. 6, a tubular spring element 143 that has an outer surface 145 that has a chemical 147 coating sensitive to the physical and chemical property undergoing detection. The interior surfaces 148 of the tube may have a material 149 coated on part of all of the interior surface 148 that is inert or develops surface charges at a differing rate than the outer chemical coating 147, which creates a mechanical stress in the tubular spring element 143 with resulting bending. The sample 153 of the monitored media may be placed on or in close proximity to chemical 147, and the sample 153 may be placed in contact with interior surfaces 148 and material 149. The tubular microcantilever may have a length of about 1 to about 200 µm, a diameter of about 1 to about 100 µm, and a wall thickness of about 0.5 to about 50 µm. The cylindrical microcantilever may have a length of about 1 to about 200 µm, and a diameter of about 1 to about 100 µm, with no central void.

Another embodiment relates to maintaining an oscillation of spring element 3, as described in Wachter et al., U.S. Pat. No. 5,445,008. The oscillation is maintained by a piezoelectric transducer and an oscillator (not shown). The present invention can detect and monitor the temperature changes of chemical and biochemical reactions in a sample 13 placed on the chemical coating 7 of the spring element 3, by detecting and analyzing the resonance frequency of the microcantilever. Changes in resonance frequency of an oscillating spring element 3 are due to temperature changes of the coatings on the spring element, the temperature changes induced by heat transferred from chemical and biochemical reactions of biomolecules in an analyte of a sample placed on, or in close proximity to the spring element. As the coatings detect changes in heat content of the analyte, the differing coefficient of thermal expansions of the spring elements multiple materials will result in mechanical stresses that deflect the spring element 3. Deflections based on changes in heat content of the analyte will be detected in changes in the resonance frequency of the spring element 3.

Many variations will undoubtedly become apparent to one skilled in the art upon a reading of the above specification with reference to the figures. As the foregoing description is exemplary in nature, the spirit and scope of the invention should be limited only by the spirit and scope of the following appended claims.

What is claimed is:

1. An apparatus for the detection and measurement of thermodynamic changes during reversible reactions comprising:
   a) a fixed base;
   b) at least one cantilever spring element attached to said base, said spring element comprising:
      i) a flexible substrate having a low thermal mass and a first coefficient of thermal expansion;
      ii) at least one coating material on said substrate, said coating material having a different coefficient of thermal expansion;
      iii) a biomaterial applied to said at least one coating material, said biomaterial being reversibly reactive with at least one analyte; and
   c) means to detect and measure deflection of said at least one cantilevered spring element.

2. An apparatus according to claim 1 wherein the biomaterial is selected from the group consisting of peptides, proteins, enzymes, nucleic acid probes, carbohydrates, antigens, antibodies, immobilized pharmaceuticals, sulfur-containing molecules, heavy metals and linkers connecting said coating material to said biomaterial.

3. An apparatus according to claim 1 further comprising a second coating material on a side of said flexible substrate opposite of said first coating material and having a coefficient of thermal expansion different from said first coating material.

4. An apparatus according to claim 1 wherein said fixed base is a piezoelectric transducer.

5. An apparatus according to claim 1 further comprising a heating element within or upon said at least one cantilevered spring element.

6. The apparatus as described by claim 1, wherein said at least one coating material is selected from the group consisting of gold, copper, aluminum, polymers, silicon nitride, and silicon compounds.

7. The apparatus as described by claim 1, wherein said flexible substrate is composed of a material selected from the group consisting of ceramics, polymers, quartz, silicon nitride, silicon, silicon oxide, silicon nitride, aluminum oxide, tantilum pentoxide, germanium, germanium dioxide, gallium arsenide, zinc oxide, and silicon compounds.

8. The apparatus as described by claim 1 wherein said at least one cantilever spring element comprises a microcantilever, said microcantilever having a length of about 1 to about 200 µm, a width of about 1 to about 50 µm, and a thickness of about 0.3 to about 3.0 µm.

9. The apparatus as described by claim 1 further comprising a reference cantilever spring element in close proximity to said base, said reference cantilever having a length of about 1 to about 200 µm, a width of about 1 to about 50 µm, and a thickness of about 0.3 to about 3.0 µm.

10. The apparatus as described by claim 1, wherein said means to detect and measure deflection comprises:
   a reflective region on said spring element;
   a laser light source positioned to direct light at said reflective region of said spring element;
   a light sensitive detector positioned to receive reflected light from reflective region of said spring element; and
   a microprocessor for determining the deflection of said spring element.

11. The apparatus as described by claim 1, wherein said means to detect and to measure deflection comprises one of a laser detecting means, a piezoresistive detecting means, a piezoelectric detecting means, a capacitive detecting means, and an electron tunneling detecting means.

12. The apparatus as described by claim 1, wherein said cantilever spring element further comprises a cylindrical microcantilever having a length of about 1 to about 200 µm, and a diameter of about 1 to about 100 µm.

13. The apparatus as described by claim 12, wherein said cylindrical microcantilever comprises a tubular microcantilever having a wall thickness of about 0.5 to about 50 µm.

14. A method for the detection and measurement of thermodynamic changes during reversible reactions comprising:
   a) providing a fixed base, at least one cantilevered spring element attached to said base, said spring element comprising i) a flexible substrate having a low thermal mass and a first coefficient of thermal expansion; ii) at least one coating material on said substrate, said coating material having a different coefficient of thermal expansion, and iii) a biomaterial applied to said at least one coating material, said biomaterial being reversibly reactive with at least one analyte; b) providing means to detect and measure the deflection of said at least one cantilevered spring element and c) bringing said cantilevered spring element into a medium which contains a molecular species reversibly reactive with said biomaterial; and d) measuring the movement of the cantilever.

15. A method according to claim 14 wherein the biomaterial is selected from the group consisting of peptides, proteins, enzymes nucleic acid probes, carbohydrates, antigens, antibodies, immobilized pharmaceuticals, sulfur-containing compounds and heavy metals.

16. A method according to claim 15 wherein the thermodynamic change measured is a binding of said biomaterial and said analyte.

17. A method according to claim 15 wherein the thermodynamic change measured is the displacement of a bound partner from said biomaterial.

18. A method according to claim 14 wherein the thermodynamic change measured is a chemical change in the analyte.

19. A method according to claim 14 wherein the movement which is measured is transient.

20. A method according to claim 14 wherein the movement of the cantilever is from a first to a second stable position.

21. A method according to claim 14 further comprising a fixed base which is a piezoresistive transducer and the thermodynamic change is measured as a change in the resonance frequency of the cantilever.

22. A method according to claim 14 wherein said cantilevered spring element is heated and the movement is measured at a specified temperature.

23. A method according to claim 14 wherein the cantilevered spring element is heated and the movement of the cantilevered spring element is measured as the temperature of the cantilevered spring element is pulsed.

24. A method according to claim 14 wherein the medium is a gas.

25. A method according to claim 14 wherein the medium is a liquid.

* * * * *